United States Patent [19]

Kobayashi

[11] Patent Number: 5,120,863

[45] Date of Patent: Jun. 9, 1992

[54] PROCESS FOR PREPARATION OF DIACETAL COMPOUNDS

[75] Inventor: Toshiaki Kobayashi, Nara, Japan

[73] Assignee: New Japan Chemical Co., Ltd., Kyoto, Japan

[21] Appl. No.: 590,769

[22] Filed: Sep. 26, 1990

[30] Foreign Application Priority Data

Oct. 2, 1989 [JP] Japan .................................. 1-258419

[51] Int. Cl.$^5$ ............................................ C07D 323/04
[52] U.S. Cl. ..................................... 549/364; 549/362
[58] Field of Search ................................. 549/362, 364

[56] References Cited

U.S. PATENT DOCUMENTS

| 4,444,766 | 4/1984 | Bossies et al. | 558/169 |
| 4,459,418 | 7/1984 | Greenshields | 549/374 |
| 4,562,265 | 12/1985 | Machell | 549/364 |
| 4,804,769 | 2/1989 | Solarek et al. | 549/374 |
| 4,902,807 | 2/1990 | Kobayashi et al. | 549/364 |

*Primary Examiner*—C. Warren Ivy
*Assistant Examiner*—Raymond Covington
*Attorney, Agent, or Firm*—Larson and Taylor

[57] ABSTRACT

Disclosed is a process for preparing a diacetal compound such as a dibenzylidene sorbitol, comprising the steps of (i) condensing an aldehyde compound and a polyhydric alcohol in the presence of an acid catalyst and when required a lower alcohol in a hydrophobic organic solvent to give a reaction mixture containing a diacetal compound, (ii) neutralizing the reaction mixture, (iii) washing the mixture with water, (iv) removing the solvent from the mixture thus washed, and (v) drying the residual mass; the process being characterized in that an amine such as, for example, di($C_{10}$–$C_{26}$ alkyl or alkenyl)amine substituted on the nitrogen atom with a $C_1$–$C_4$ alkyl group or with a group of the formula ⟨$C_2H_4O$⟩$_q$H wherein q is an integer of 1 to 4, or a ($C_{14}$–$C_{22}$ alkyl or alkenyl)amine sustituted on the nitrogen atom with one or two groups of the formula ⟨$C_2H_4O$⟩$_q$H wherein q is 1 to 4, is added during the period from the formation of the reaction mixture to the completion of the drying step.

12 Claims, No Drawings

PROCESS FOR PREPARATION OF DIACETAL COMPOUNDS

The present invention relates to a commercially advantageous process for preparing diacetal compounds, and more particularly to a process for preparing diacetal compounds which is capable of producing diacetal compounds free from hydrolysis, and from the coloration of diacetal and emission of offensive odor which would be caused by the hydrolysis.

The diacetal compounds of the formula (1) given below are substances having unique properties and have a wide variety of uses:

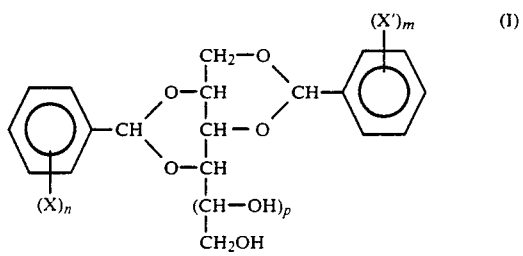

wherein X and X' are the same or different and each represent a hydrogen atom, a halogen atom, an alkyl group having 1 to 4 carbon atoms, an alkylthio group having 1 to 4 carbon atoms, or an alkoxy group having 1 to 4 carbon atoms, m and n are the same or different and each represent an integer of 1 to 5, and p is 0 or 1. For example, such diacetal compounds are useful as transparency improving agents for polypropylene and other resins, as flowability improving agents for paints, inks, adhesives and other compositions, and solidifying agents for adhesives, cosmetics, pharmaceuticals and so forth.

These diacetal compounds are prepared by condensing an aromatic aldehyde and a polyhydric alcohol in the presence of an acid catalyst (and if desired a lower alcohol) in a hydrophobic organic solvent, neutralizing the acid catalyst, washing the reaction mixture with water, removing the solvent, and drying the residue (Japanese Examined Patent Publications No.43,748/1973, No.22,156/1983 and No.22,157/1983, Japanese Unexamined Patent Publication No.149,789/1989, U.S. Pat. No.4,902,807, etc.).

These processes, although capable of giving the contemplated diacetal compounds in high yields, tend to form solids or gel-like blocks, i.e. agglomerates of diacetal compounds, during the production. The agglomerates contain locally non-neutralized acid catalyst therein even after the neutralization. The remaining catalyst causes the hydrolysis of diacetal (condensation product) by heating after the neutralizing step, e.g., during the solvent-removing step and the drying step. The local hydrolysis of diacetal is considered responsible for not only a reduced yield of diacetal compounds but also the coloration thereof and the odor given off due to the unreacted aldehyde as well as the aldehyde used as the starting material.

The development of techniques for preventing the coloration and emission of odor is desired especially in the fields in which molded products of resins formed with a diacetal as a nucleating agent are used as packaging materials or containers for foods and clothes. Among the techniques capable of obviating the foregoing problems, a method is known in which a diacetal is treated with a fluid in a high pressure gas-liquid critical state, i.e., supercritical state or near the critical state for purification (Japanese Unexamined Patent Publication No.199,891/1985). The method, however, is not invariably commercially advantageous because of the need to use and maintain additional equipment for the above special purification.

It is an object of the present invention to provide a commercially advantageous process for preparing a diacetal compound in high yields, the process being substantially unlikely to color the diacetal compound and to cause offensive odor due to the aldehyde formed by the hydrolysis.

According to the present invention, there is provided a process for preparing a diacetal compound, the process comprising the steps of:
(i) condensing (A) an aldehyde compound represented by the formula

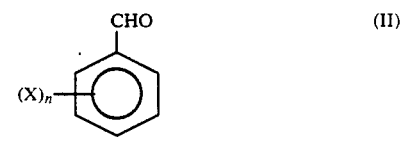

wherein X is a hydrogen atom, a halogen atom, an alkyl group having 1 to 4 carbon atoms, an alkylthio group having 1 to 4 carbon atoms, or an alkoxy group having 1 to 4 carbon atoms, and n is an integer of 1 to 5, or an aldehyde compound represented by the formula

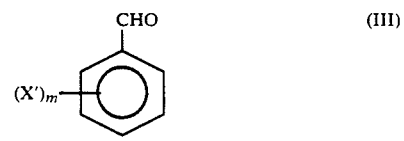

wherein X' is a hydrogen atom, a halogen atom, an alkyl group having 1 to 4 carbon atoms, an alkylthio group having 1 to 4 carbon atoms or an alkoxy group having 1 to 4 carbon atoms, and m is an integer of 1 to 5, or a mixture of the aldehyde compounds of the formulas (II) and (III), and (B) a polyhydric alcohol represented by the formula

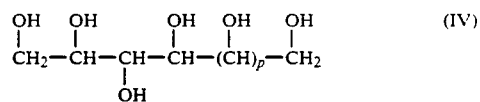

wherein p is 0 or 1, in the presence of an acid catalyst and when required a lower alcohol in a hydrophobic organic solvent to give a reaction mixture containing a distal compound represented by the formula

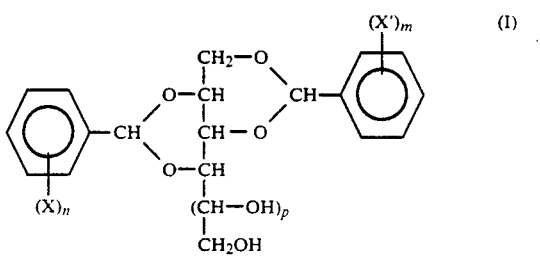

wherein X, X' and p are as defined above, (ii) neutralizing the reaction mixture,
(iii) washing the mixture with water,
(iv) removing the solvent from the mixture thus washed, and
(v) drying the residual mass;

the process being characterized in that an amine represented by the formula

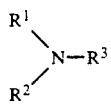 (1)

wherein $R^1$ and $R^2$ are the same or different and each represent an alkyl or alkenyl group having 10 to 26 carbon atoms, and $R^3$ is an alkyl group having 1 to 4 carbon atoms or $-(C_2H_4O)_qH$ wherein q is an integer of 1 to 4, or an amine represented by the formula

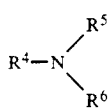 (2)

wherein $R^4$ is an alkyl or alkenyl group having 14 to 22 carbon atoms, and $R^5$ and $R^6$ are the same or different and each represent a hydrogen atom or $-(C_2H_4O)_qH$ wherein q is an integer of 1 to 4, provided that both of $R^5$ and $R^6$ do not represent a hydrogen atom at the same time, or a mixture of the amine of the formula (1) and the amine of the formula (2) is added at an optional time during the period from the formation of the reaction mixture to the completion of the drying step.

We conducted extensive research to develop a novel process for preparing a diacetal compound which is capable of meeting said object in a simpler manner without a special purification procedure, and found that the local hydrolysis of diacetal which has been hitherto difficult to avoid can be prevented by adding the aliphatic amine of the formula (1) and/or (2) each having the above specific structure, whereby the contemplated object can be achieved. The present invention has been accomplished on the basis of this novel finding.

The diacetal compounds of the formula (I) prepared by the process of the present invention include those of the asymmetry type wherein the substituents on the two benzene rings are not identical in the kind and the number and those of the symmetry type wherein the substituents on the two benzene rings are identical in the kind and the number, and mixtures of these compounds.

The aromatic aldehydes usable in the invention are represented by the formula (II) and the formula (III):

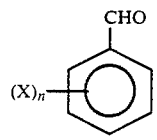 (II)

wherein X and n are as defined above in the formula (I), and

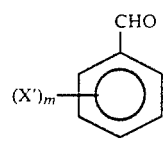 (III)

wherein X' and m are as defined above in the formula (I).

Specific examples of these aldehydes are benzaldehyde, benzaldehyde substituted with 1 to 5 alkyl groups of 1 to 4 carbon atoms, benzaldehyde substituted with 1 to 5 alkylthio groups of 1 to 4 carbon atoms, benzaldehyde substituted with 1 to 5 halogen atoms, benzaldehyde substituted with 1 to 5 alkoxy groups of 1 to 4 carbon atoms, and mixtures of such aldehydes in an optional ratio. The preferred number of the substituents is 1, 2 or 3.

The polyhydric alcohol for use in the invention is represented by the formula

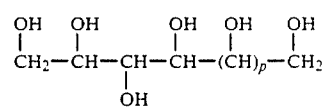 (IV)

wherein p is as defined above in the formula (I).

Examples of useful polyhydric alcohols are sorbitol, xylitol and like sugar alcohols, and mixtures of the alcohols in an optional ratio.

Examples of useful acid catalysts are sulfuric acid, phosphoric acid, p-toluenesulfonic acid, m-toluenesulfonic acid, alkyl($C_2$-$C_{12}$)benzenesulfonic acid, G acid, R acid, zinc chloride, etc.

Representative lower alcohols are saturated aliphatic alcohols having 1 to 4 carbon atoms, such as methanol, ethanol, propanol, butanol and the like, and furfuryl alcohols, etc.

Examples of suitable hydrophobic organic solvents are benzenes optionally substituted with lower alkyl groups of 1 to 4 carbon atoms such as benzene, toluene, xylene, etc.; saturated aliphatic hydrocarbons having 6 to 18 carbon atoms such as hexane, heptane, decane, etc.; and cyclohexanes optionally substituted with lower alkyl group of 1 to 4 carbon atoms such as cyclohexane, methylcyclohexane, ethylcyclohexane, etc.

The aliphatic amines usable in the invention are an amine represented by the formula (1) and the formula (2):

 (V)

wherein $R^1$ and $R^2$ are the same or different and each represent an alkyl or alkenyl group having 10 to 26 carbon atoms, and $R^3$ is an alkyl group having 1 to 4 carbon atoms or $-(C_2H_4O)_qH$ wherein q is an integer of 1 to 4, and an amine represented by the formula

 (VI)

wherein $R^4$ is an alkyl or alkenyl group having 14 to 22 carbon atoms, and $R^5$ and $R^6$ are the same or different and each represent a hydrogen atom or $-(C_2H_4O)_qH$ wherein q is an integer of 1 to 4, provided that both of $R^5$ and $R^6$ do not represent a hydrogen atom at the same time.

Preferred examples of the aliphatic amines of the formula (V) are $di(C_{10}-C_{26}$ alkyl or alkenyl)amine substituted on the nitrogen atom with an $C_1-C_4$ alkyl group or with a group of the formula $-(C_2H_4O)_qH$ wherein q is an integer of 1 to 4, such as distearylmethylamine, dihexadecylmethylamine, ditetradecylmethylamine, didodecylmethylamine, dioleylmethylamine, stearyllaurylmethylamine, distearylethylamine, dioleylpropylamine, dilaurylbutyl-amine, distearylhydroxyethylamine, an adduct of dioleylamine with 2 moles of ethylene oxide, an adduct of distearylamine with 4 moles of ethylene oxide, etc.

Preferred examples of the aliphatic amines of the formula (VI) are $C_{14}-C_{22}$ alkylamine or $C_{14}-C_{22}$ alkenylamine each substituted on the nitrogen atom with one or two groups of the formula $-(C_2H_4O)_qH$ wherein q is an integer of 1 to 4, such as tetradecylhydroxyethylamine, stearylhydroxyethylamine, an adduct of stearylamine with 2 moles of ethylene oxide, N-(hydroxyethyloxyethyl)oleylamine and the like, and tetradecyldi(hydroxyethyl)amine, hexadecyldi(hydroxyethyl)amine, stearyldi(hydroxyethyl)-amine, oleyldi(hydroxyethyl)amine and the like.

Of the two types of amines, the amines of the formula (V) are preferred because they can more effectively inhibit the hydrolysis of diacetal compounds of the formula (I) than the amines of the formula (VI).

In the process of the invention, the condensation reaction between the aldehyde compound of the formula (II) and/or (III) and the polyhydric alcohol of the formula (IV) may be conducted by conventional methods such as any of those as disclosed in Japanese Examined Patent Publications No.43,748/1973, No.22,156/1983 and No.22,157/1983, Japanese Unexamined Patent Publication No.149,789/1989, U.S. Pat. No.4,902,807, etc.

According to one preferred embodiment of the invention, the condensation reaction is performed by the method described in Japanese Unexamined Patent Publication No.149789/1989.

The condensation reaction gives a reaction mixture containing a diacetal compound of the formula (I). It is critical in the invention to add the aliphatic amine of the formula (1) and/or (2) at an optional time during the period after the condensation reaction and prior to the completion of the drying step.

These aliphatic amines are usable singly or at least two of them can be used in mixture. The amount of the aliphatic amine to be used is about 0.1 to about 20 parts by weight, preferably about 0.3 to about 13 parts by weight, per 100 parts by weight of the diacetal. If less than 0.1 part by weight of the aliphatic amine is used, a satisfactory degree of the desired effect can not be easily produced. If the amount exceeds 20 parts by weight, a pronouncedly excellent result can not be obtained, and disadvantageously the amine tends to become colored itself during heating, consequently resulting in coloring of diacetal. Thus the use of the amine in an amount outside the above range is undesirable.

The point of time for adding the amine is not specifically limited insofar as it is after the completion of the condensation reaction. Stated more specifically, the desired effect can be obtained by adding the amine in any of the steps after the condensation reaction step, namely in one of the neutralization step, the washing step, the solvent-removing step and the drying step, or optionally at a time after the completion of one of the neutralization step, the washing step and the solvent-removing step and before the initiation of the next step. The amine is preferably added at the foremost stage, namely in the neutralization step, in order to more effectively prevent the hydrolysis of diacetal.

The amine added at the neutralization step acts as a neutralizing agent for the acid catalyst, and can be used singly or in mixture with an aqueous solution or a lower alcohol solution of sodium hydroxide, potassium hydroxide or like alkali metal hydroxide which is conventionally used in the art as a neutralizing agent.

The method of adding the amine is not specifically limited insofar as it can produce the desired effect. Typically, a solution containing about 1 to about 40% by weight of the amine in a solvent is added to the diacetal, and the mixture is homogeneously stirred and dried.

Solvents suitable for the preparation of said solution are good solvents capable of dissolving the amines well. Representative solvents are benezene, toluene, xylene, n-hexane, cyclohexane, n-decane, mineral spirit and like aliphatic, alicyclic and aromatic hydrocarbons; isopropanol, ethanol/isopropanol mixture and like lower $(C_1-C_4)$alcohols; allyl alcohols; methyl chloride, trichloroethylene, perchloroethylene and like halogenated hydrocarbons having 1 to 4 carbon atoms; etc. Among them, cyclohexane, lower alcohols and the like are preferred.

According to a preferred embodiment of the invention, the process of the invention is carried out, for example, by conducting the steps (1) to (5) as described below.

(1) Condensation Reaction Step

This step is preferably conducted by the method disclosed in Japanese Unexamined Patent Publication No.149,789/1989. In short, the method is as follows.

The aldehyde compound (A) of the formula (II) and/or (III), the polyhydric alcohol (B) of the formula (IV), a lower alcohol serving as an auxiliary solvent and an acid catalyst are mixed and stirred at a temperature ranging from room temperature to about 60° C. to give a homogeneous mixture or suspension. The condensation reaction is conducted while continuously or intermittently feeding into a reactor said homogeneous mixture or suspension and a hydrophobic organic solvent serving as a dispersing medium.

Reactors usable in the above reaction include those commonly employed in the art, such as a reactor equipped with a condenser having a decanter, a thermometer, a stirrer, a gas inlet, etc. A preferred ratio of the aldehyde compound (A) of the formula (II) and/or (III) to the polyhydric alcohol (B) of the formula (IV) is approximately from 1 : 1 to 4 : 1, and particularly from 1.5 : 1 to 3 : 1. The aldehyde compound (A) and the polyhydric alcohol (B) will be hereinafter collectively referred to as "reaction substrate". The amount of the lower alcohol to be used is about 10 to about 500 parts by weight, preferably about 50 to about 200 parts by weight, per 100 parts by weight of the reaction substrate. The amount of the acid catalyst to be used is about 0.05 to about 10 parts by weight, preferably about 0.2 to about 5 parts by weight, per 100 parts by weight of the reaction substrate. The concentration (% by weight) of the reaction substrate (C), which is represented by the equation (1)

$$C = \frac{S}{S + H} \times 100 \quad (1)$$

wherein S represents the weight of the reaction substrate and H represents the weight of the hydrophobic organic solvent, can be suitably selected from a wide range of about 5% to about 90% by weight. The reaction system can be made into any form such as a low-viscosity slurry, paste, powder, etc. by selection of a concentration of the reaction substrate which can be done by adjusting the amount of the hydrophobic organic solvent according to the shape of the reactor to be used and the like.

The reaction is conducted at a temperature of about 40° to about 200° C. for about 2 to about 15 hours. During the reaction, the lower alcohol, hydrophobic organic solvent and water formed upon condensation reaction are distilled off by vapor-liquid equilibrium or in the form of an azeotropic mixture. The distillate is separated by the decanter into a water/lower alcohol layer and a hydrophobic organic solvent layer. The water/lower alcohol layer is drawn off outside the reaction system, and the hydrophobic organic solvent layer is recycled into the reaction system.

The reaction gives a reaction mixture in the form of a slurry or wet powder.

(2) Neutralization Step

The reaction mixture in the form of a slurry or wet powder is filtered when required, and the above-specificed amount of the aliphatic amine of the formula (V) and/or (VI) or a solution of the amine prepared beforehand is added to the mass, preferably together with a solution (an aqueous solution or a lower alcohol solution) of a strong base such as sodium hydroxide to completely neutralize the acid catalyst. The action of the foregoing amine is not fully clarified, but it may be presumed that the amine used in the invention permeates into the agglomerates or gel-like blocks more readily than the strong base such as sodium hydroxide, whereby the neutralization is accelerated, and thus the amount of remaining acid component is reduced.

(3) Washing Step

The mixture is washed with water at a temperature between room temperature and about 90° C. to remove salts formed, unreacted materials such as polyhydric alcohol and aromatic aldehyde as well as reaction intermediates such as monobenzal and the like. During the washing step, the aliphatic amine of the formula (V) and/or (VI) added in the preceding step is hydrophobic and therefore remains in the system except for one removed as an acid catalyst-amine complex.

(4) Solvent-removing Step

The solvent, particularly the hydrophobic organic solvent is removed with heating at about 40° to about 180° C. at atmospheric pressure or reduced pressure (about 760 to about 1 mmHg).

(5) Drying Step

The residual mass formed upon removal of the solvent usually contains water and is dried with heating and/or at normal or reduced pressure. The heating may be performed at a temperature of about 40 to about 180° C. The pressure during the drying step may range from about 760 to about 1 mmHg.

The thus obtained diacetal compound is substantially free of offensive odor given off due to the remaining aldehyde and has a desired color and a notably improved thermal stability.

The diacetal compounds of the present invention are usable not only as a nucleating agent for crystalline resins but also as gelling agents for liquid materials, viscosity modifiers, thixotropic agents, anti-sagging agents, oil/water separating agents, flocculating agents or the like, and can be used in the fields in which the diacetal compounds prepared in the conventional processes have been heretofore used, for example, in the fields of modifiers for adhesives, paints or resins, perfumes, water treatment, solidification and recovery of leaked oils, cosmetics, construction and building materials, lubricants, corrosion inhibitors, agricultural chemicals, pharmaceuticals, non-pharmaceutical products, fuel, inks, pastes, etc.

The present invention will be described below in greater detail with reference to the following Examples and Comparative Example. In each Example and Comparative Example, the properties of the obtained product were evaluated according to the following procedures.

(a) Purity (% by weight): determined by gas chromatography
(b) Amount of aldehyde (ppm): determined by gas chromatography after Soxhlet extraction
(c) Color: 10 wt.% solution in N-methyl-2-pyrrolidone was rated for color according to American Public Health Association (APHA) method

EXAMPLE 1

A mixture of 20 kg of sorbitol, 27 kg of p-tolualdehyde (p-tolualdehyde/sorbitol molar ratio = 2.1) and 27 kg of methanol was heated at 50° C. with stirring in the presence of 0.3 kg of sulfuric acid to give a homogeneous solution.

A 200-liter reactor equipped with a stirrer and a decanter-equipped condenser was fed with 7 l of the above homogeneous solution and 9 l of cyclohexane (via a separate line) and the contents in the reactor were agitated at 70° C.

Thereafter, while the homogeneous solution was continuously fed to the reactor over a period of 3 hours, cyclohexane was continuously placed into the reactor (via a separate line) at a rate such that the concentration of the reaction substrate in the reaction system was always adjusted to a constant level of 35% by weight. The reaction was conducted with heating at 65 to 75° C. over a period of 5 hours. During the reaction, the cyclohexane in the distillate was recycled to the reaction system and the mixture of water and methanol in the distillate was removed from the reaction system.

To the reaction mixture in the form of a paste thus obtained were added 8 kg of a 5 wt.% solution of distearyl methylamine in cyclohexane and 1 kg of a 15 wt.% aqueous solution of sodium hydroxide to neutralize the reaction system. The resulting mixture was washed with 50 l of warm water and heated at a temperature of 80 to 120° C. under a pressure of 760 to 10 mm.Hg for 10 hours for removing the solvent and for drying, giving 1,3:2,4ditolylidenesorbitol (hereinafter briefly referred to as "Me-DBS") having a purity of 99.5% by weight in a yield of 90% by weight. The product contained aldehydes in an amount of 50 ppm and had a color (APHA) of 50.

EXAMPLE 2

The same procedure as in Example 1 was repeated with the exception of using di(hydroxyethyl)stearylamine as an aliphatic amine, giving Me-DBS (purity=99.5%, yield=89% by weight). The product contained aldehydes in an amount of 55 ppm and had a color (APHA) of 55.

EXAMPLE 3

The same procedure as in Example 1 was repeated with the exception of using a mixture of stearyl lauryl methylamine and stearyl hydroxyethylamine (weight ratio of 1:1), giving Me-DBS (purity=99.5%, yield=90% by weight). The product thus obtained contained aldehydes in an amount of 40 ppm and had a color (APHA) of 40.

EXAMPLE 4

The reaction mixture in the form of a paste obtained in Example 1 was neutralized with a 10 wt.% solution of potassium hydroxide in isopropanol/water and washed with water. To the reaction product thus neutralized and washed was added 40 kg of a 10 wt.% solution of distearyl methylamine in a 1:1 (by weight) mixture of isopropanol and methanol, followed by stirring for 100 minutes to give a mixture. The mixture obtained was heated for removing the solvent and for drying under the same conditions as in Example 1, giving Me-DBS (purity =99.5%, yield=88% by weight). The product contained aldehydes in an amount of 30 ppm and had a color (APHA) of 50.

EXAMPLE 5

The same procedure as in Example 1 was repeated with the exception of using 23.9 kg of benzaldehyde in place of p-tolualdehyde, giving 1,3:2,4-dibenzylidenesorbitol. The product thus obtained contained aldehydes in an amount of 1 ppm and had a color (APHA) of 30.

COMPARATIVE EXAMPLE 1

The same procedure as in Example 1 was repeated except that distearyl methylamine was not used, giving MeDBS. The product contained aldehydes in an amount of 750 ppm and had a color (APHA) of 280.

I claim:
1. A process for preparing a diacetal compound, the process comprising the steps of:
  (i) condensing (A) an aldehyde compound represented by the formula

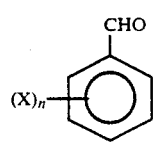

wherein X is a hydrogen atom, a halogen atom, an alkyl group having 1 to 4 carbon atoms, an alkylthio group having 1 to 4 carbon atoms, or an alkoxy group having 1 to 4 carbon atoms, and n is an integer of 1 to 5, or an aldehyde compound represented by the formula

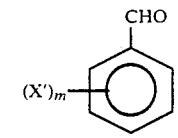

wherein X' is a hydrogen atom, a halogen atom, an alkyl group having 1 to 4 carbon atoms, an alkylthio group having 1 to 4 carbon atoms or an alkoxy group having 1 to 4 carbon atoms, and m is an integer of 1 to 5, or a mixture of the aldehyde compounds of the formulas (II) and (III) and (B) a polyhydric alcohol represented by the formula

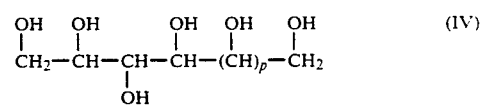

wherein p is 0 or 1, in the presence of an acid catalyst and when required a lower alcohol in a hydrophobic organic solvent to give a reaction mixture containing a diacetal compound represented by the formula

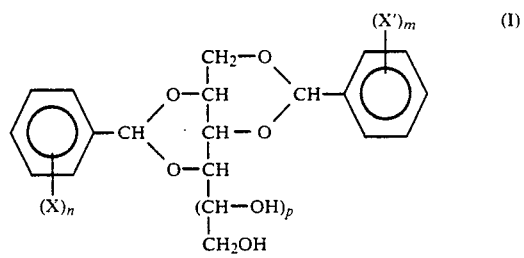

wherein X, X', p, m and n are as defined above,
  (ii) neutralizing the reaction mixture,
  (iii) washing the mixture with water,
  (iv) removing the solvent from the mixture thus washed, and
  (v) drying the residual mass;
the process being characterized in that an amine represented by the formula

wherein $R^1$ and $R^2$ are the same or different and each represent an alkyl or alkenyl group having 10 to 26 carbon atoms, and $R^3$ is an alkyl group having 1 to 4 carbon atoms or $\text{---}(C_2H_4O)_q H$ wherein q is an integer of 1 to 4; or an amine represented by the formula

wherein $R^4$ is an alkyl or alkenyl group having 14 to 22 carbon atoms, and $R^5$ and $R^6$ are the same or different and each represent a hydrogen atom or $\text{---}(C_2H_4O)_q H$ wherein q is an integer of 1 to 4, provided that both of $R^5$ and $R^6$ do not represent a hydrogen atom at the same time; or a mixture of the amine of the formula (V) and the amine of the formula (VI) is added at any time after the completion of the condensation step (i) but before the completion of the drying step (v).

2. A process according to claim 1 wherein the amine of the formula (V) is used.

3. A process according to claim 1 wherein the amine of the formula (VI) is used.

4. A process according to claim 1 wherein the amine of the formula (V) is at least one member selected from the group consisting of distearylmethylamine, dihexadecylmethylamine, ditetradecylmethylamine, didodecylmethylamine, dioleylmethylamine, stearyllaurylmethylamine, distearylethylamine, dioleylpropylamine, dilaurylbutylamine, distearylhydroxyethylamine, an adduct of dioleylamine with 2 moles of ethylene oxide, and an adduct of distearylamine with 4 moles of ethylene oxide.

5. A process according to claim 1 wherein the amine of the formula (VI) is at least one member selected from the group consisting of tetradecylhydroxyethylamine, stearylhydroxyethylamine, an adduct of stearylamine with 2 moles of ethylene oxide, tetradecyldi(hydroxyethyl)amine, hexadecyldi(hydroxyethyl)amine, stearyldi(hydroxyethyl)-amine and oleyldi(hydroxyethyl)amine.

6. A process according to claim 1 wherein about 0.1 to about 20 parts by weight of the amine of the formula (V), the amine of the formula (VI) or a mixture of these amines is added per 100 parts by weight of the diacetal compound of the formula (I).

7. A process according to claim 1 wherein about 0.3 to about 13 parts by weight of the amine of the formula (V), the amine of the formula (VI) or a mixture of these amines is added per 100 parts by weight of the diacetal compound of the formula (I).

8. A process according to claim 1 wherein a solution of the amine of the formula (V), the amine of the formula (VI) or a mixture of these amines in a solvent capable of dissolving the amine well at a concentration of about 1 to about 40% by weight is added.

9. A process according to claim 8 wherein the solvent is at least one solvent selected from the group consisting of aliphatic, alicyclic and aromatic hydrocarbons, lower alcohols, and halogenated hydrocarbons.

10. A process according to claim 1 wherein the amine of the formula (V), the amine of the formula (VI) or a mixture of these amines is added in the neutralization step.

11. A process according to claim 1 wherein a solution of the amine of the formula (V), the amine of the formula (VI) or a mixture of these amines in a solvent capable of dissolving the amine well at a concentration of about 1 to 40% by weight is added in the neutralization step.

12. A process according to claim 1 wherein the amine of the formula (1), the amine of the formula (2) or a mixture of these amines is added on completion of the washing step.

* * * * *